United States Patent [19]

Band et al.

[11] Patent Number: 4,777,278

[45] Date of Patent: Oct. 11, 1988

[54] SYNTHESIS OF ALKYL CYCLOALKYL DIALKOXYSILANES

[75] Inventors: Elliot I. Band, North Tarrytown, N.Y.; Suzanne T. Eberhart, New Haven, Conn.

[73] Assignee: Akzo America Inc., New York, N.Y.

[21] Appl. No.: 105,749

[22] Filed: Oct. 8, 1987

[51] Int. Cl.$^4$ .............................. C07F 7/08; C07F 7/18
[52] U.S. Cl. ..................................... 556/480; 556/470
[58] Field of Search ......................................... 556/480

[56] References Cited

U.S. PATENT DOCUMENTS

| | | | |
|---|---|---|---|
| 2,380,057 | 7/1945 | McGregor et al. | 556/480 |
| 2,442,053 | 5/1948 | McGregor et al. | 556/480 |

FOREIGN PATENT DOCUMENTS 1162808  6/1985  U.S.S.R. .............................. 556/480

OTHER PUBLICATIONS

V. Bazant et al., Organosilicon Compounds, vol. 2$^1$, Academic Press, 1965, pp. 8, 350, and 482.
Chemical Abstracts, vol. 52, 16188a.
S. Chrzczonowicz et al., Roczniki Chem., vol. 32, 155–157, (1958).
Chemical Abstracts, vol. 61, 13339a.
Z. Lasocki, Bull. Acad. Polon. Sci., Ser. Sci. Chim., 12(5), 281–287, (1964).
V. Bazant et al., Organosilicon Compounds, vol. 1, Academic Press, 1965, pp. 184–186, 418, 425, 395, and 386.
Chemical Abstracts, vol. 56, 7344h, (1962).
S. Chrzczonowicz et al., Roczniki Chem., 34, 1667–1674, (1960).
Chemical Abstracts, vol. 47, 2724g.
J. Amer. Chem. Soc., vol. 77, pp. 6647–6649, (Dec. 20, 1955).

*Primary Examiner*—Paul F. Shaver
*Attorney, Agent, or Firm*—Richard P. Fennelly; Louis A. Morris

[57] ABSTRACT

Alkyl cycloalkyl dialkoxysilanes (e.g., methyl cyclohexyl dimethoxysilane) can be prepared by reaction of an alkyl trialkoxysilane (e.g., methyl trimethoxysilane) with a Grignard reagent containing the cycloalkyl moiety derived in the final end-product (e.g., a reagent formed by reacting cyclohexyl chloride and magnesium metal). The reaction is run in the absence of ether solvent, the Grignard reagent is preferably formed in situ by the reaction of magnesium metal and cyclohexyl halide, and agitation is used to promote the reaction. Advantageously, a catalyst, such as iodine, is used to promote the reaction.

11 Claims, No Drawings

SYNTHESIS OF ALKYL CYCLOALKYL DIALKOXYSILANES

BACKGROUND OF THE PRESENT INVENTION

1. Field of the Invention

The present invention is a novel process for the synthesis of alkyl cycloalkyl dialkoxysilanes.

2. Description of the Prior Art

V. Bazant et al., in Organosilicon Compounds, Vol. 2[1] (1965) on pages 8, 350 and 482 names methyl cyclohexyl dimethoxysilane and appears to indicate its synthesis by a Grignard route by citation of an article by S. Chrzczonowicz et al. in Rocniki Chemii, Vol. 32, 155-157 (1958) which is abstracted in Chemical Abstracts, Vol. 52, 16188a (1958). A closer examination of the disclosure of this cited reference, however, indicates that the content of this publication is limited to the hydrolysis of dialkyldimethoxysilanes.

Z. Lasocki in Bull. Acad. Polon. Sci., Ser. Sci. Chim. 12(5) 281-287 (1964), abstracted at Chemical Abstracts, 61, 13339a, mentions the Grignard synthesis of methyl cyclohexyl dimethoxysilane in only 40% yield, apparently from silicon tetrachloride or from trichloromethylsilane using an ethyl ether solvent.

S. Chrzczonowicz et al. in Roczniki Chemii, Vol, 34, 1667-1774 (1960), abstracted in Chemical Abstracts, Vol. 56, 7344h indicates the formation of methyl cyclohexyl dimethoxysilane from tetramethylsilicate by a Grignard reaction in an ether solvent.

None of the aforementioned references show or clearly suggest the formation of an alkyl cycloalkyl dialkoxysilane, in the absence of an ether solvent, from an alkyl trialkoxysilane (as contrasted to use of silicon tetrachloride, trichloromethylsilane, or tetramethylsilicate) with a Grignard reagent containing the cycloalkyl group intended in the final product.

The use of alkyl trialkoxysilane starting materials in a Grignard synthesis is mentioned by V. Bazant et al. (in Organosilicon Compounds, Vol. 1, pp. 184-185) who indicate that alkoxysilane starting materials have certain advantages over the use of chlorosilanes: their greater stability towards hydrolysis and the fact that the reaction can be carried out without solvent. However, the yield of product is said to be generally lower and the steric effects are said to be more important than in the halogenosilanes. On page 185 Bazant et al. cites as "CJ-6" the preparation of methyl phenyl diethoxysilane in yields of 60-66% by reaction of methyl triethoxysilane with chlorobenzene and magnesium metal. This work was originally reported by V. Capuccio et al., Chimico e industria (Milan) 33, 282-283 (1951) and is abstracted in Chemical Abstracts, Vol. 47, 2724g. It also fails to show or suggest Grignard synthesis of alkyl cycloalkyl dialkoxysilanes from an alkyl trialkoxysilane, since it, rather, contains an isolated disclosure of synthesis of methyl phenyl diethoxysilane.

SUMMARY OF THE PRESENT INVENTION

The present invention relates to a method of forming an alkyl cycloalkyl dialkoxysilane by reacting an alkyl trialkoxysilane with a Grignard reagent, preferably formed in situ, containing the cycloalkyl group desired in the final product. This cycloalkyl moiety substitutes for one of the alkoxy groups in the alkyl trialkoxysilane. The reaction is conducted in the absence of an ether solvent. The absence of an ether solvent eliminates the hazards associated with ethers including high flammability, toxicity, and the potential for peroxide formation. Fractional distillation of the reaction liquids is also simplified by the absence of an ether. It also decreases the solubility of the magnesium salts produced in the reaction thereby affording a purer filtrate. Further, the presence of an ether makes the magnesium salt precipitate more voluminous, hindering filtration and effective washing of the filter cake.

DETAILED DESCRIPTION OF THE PRESENT INVENTION

The alkyl trialkoxysilane starting material which is reacted with the Grignard reagent in accordance with the present invention has the formula $RSi(OR')_3$ with R and R' both being alkyl, preferably lower alkyl such as methyl or ethyl. R and R' can be the same or different. Methyl trimethoxysilane is a representative compound from this class of starting material.

The Grignard reagent has the formula $R''MgX$ where $R''$ is cycloalkyl (such as cyclohexyl) and X is halogen (such as chlorine). This reagent is preferably formed in situ by reaction of magnesium metal and cycloalkyl halide, $R''X$ so that the Grignard reagent is consumed as it is formed.

The reaction of Grignard reagent and alkyl trialkoxysilane is carried out in accordance with the present invention at elevated temperature (e.g., near reflux) using molar ratios of silane to Grignard of from about 4:1 to about 1:1 without the use of an ether solvent while attaining good yields (e.g., 70%-80% yield of methyl cyclohexyl dimethoxysilane). Non-ether solvents, such as toluene, can be used, but the reaction may also be run in the substantial absence of solvent. In order to achieve the best yields, a sufficient degree of mechanical action to continuously expose the surface of the metal and thereby promote the reaction is employed. This mechanical action can be achieved in small scale runs by using a magnetic stirrer to give the desired grinding action or by adding durable balls (e.g., glass balls) if a mechanically stirred reactor is used.

Advantageously, the reaction is promoted by using a catalytically effective amount (from about 0.001% to about 0.1%, by weight of the reactants) of a catalyst such as mercury metal, iodine and the like.

The following Examples illustrate certain embodiments of the present invention.

EXAMPLE 1

Thirty-eight grams of a solution of 2.8 grams of methyl trimethoxysilane (0.21 mole) in toluene was added to a 100 milliliter nitrogen-purged three-neck round bottom flask containing a stir bar and 0.61 gram (0.025 mole) magnesium metal powder. Cyclohexyl chloride (2.5 grams; 0.021 mole) was added at room temperature with stirring. After two hours, several crystals of iodine in toluene was added by syringe. After one-half hour the slurry was heated to 95° C. and maintained at that temperature for one hour. The slurry was then cooled and filtered. Gas chromatography showed a 59 area percent for the methyl cyclohexyl dimethoxysilane at the completion of the synthesis. The methyl cyclohexyl dimethoxysilane was 83 area percent of the products made (about 2.4 grams). The filter cake was washed once with 10 milliliters toluene.

The filtrate was vacuum stripped of toluene at ambient temperature, and the residue was distilled at 50° C., 0.5 mm Hg. Two grams of methyl cyclohexyl dimethoxysilane, 95% pure, was collected.

EXAMPLE 2

Magnesium metal (9.5 grams) was loaded into a three-neck, 250-milliliter reactor in a glove box. The reactor was set up with a stir bar, condenser, temperature probe and sampling device. All reactants were stored over molecular sieve resin, were sparged with nitrogen, and the reaction was kept under nitrogen, connected to a bubbler. Methyl trimethoxysilane (36-37 grams) was syringed into the reactor, and about 40 milligrams of iodine was added under nitrogen atmosphere. Twenty percent of the total cyclohexyl chloride charge was added initially (about 6 milliliters). The resulting slurry was stirred and heated to reflux (101°-10220 C.). After about 10-20 minutes there was an exotherm, and the slurry turned a muddy brown color. The remaining cyclohexyl chloride (24 milliliters) was added in 2-3 milliliters aliquots. After each addition there was an exotherm, and the brownish color deepened. The reaction mixture refluxed for a total of about 4-5 hours including initiation time. The reaction was judged substantially complete when the reflux temperature was about 138° C.

The slurry was then transferred through a polyethylene tube to a filter frit and was washed 5-6 times with hexane (about 10 milliliters per wash). The weight of methyl cyclohexyl dimethoxysilane product in the filter cake was about 18 grams. Gas chromatographic analysis showed that the methyl cyclohexyl dimethoxysilane was 69 area percent of the final reaction mixture and 79 area percent of the total products peaks.

EXAMPLE 3

A five-neck, 5-liter reactor was set up with a mechanical stirrer, condenser, temperature probe, sampling device, and was then purged with nitrogen. All reactants were stored over molecular sieve resin, were sparged with nitrogen, and the reaction was kept under nitrogen, connected to a bubbler. Methyl trimethoxysilane (1165 grams), magnesium metal (284 grams) and iodine (about 120 milligrams) were added to the reactor under a nitrogen atmosphere. About 15-17% of the total cyclohexyl chloride charge was added initially (about 130-150 grams). The slurry was stirred and heated to reflux. After about 10-30 minutes, there was an exotherm, and the reaction turned a muddy brown color. The remaining cyclohexyl chloride charge was added in portions through a dropping funnel under nitrogen, and the reaction was maintained at reflux. The total time at reflux was 4-5 hours including initiation time. The brown color continued to deepen as the reaction progressed. The reaction was judged substantially complete when the reflux temperature was about 138° C. Gas chromatography showed a 67 area percent for the methyl cyclohexyl dimethoxysilane (about 1000 grams) at the completion of the synthesis.

The slurry was then transferred through a polyethylene tube to a filter frit and was washed 5-6 times with hexane (about 200 milliliters/wash). The weight of hexane in the filter cake was about 500 grams. The methyl cyclohexyl dimethoxysilane product was separated by fractional distillation at a head temperature of 198° C. at atmospheric pressure. About 93% of the desired silane product that was made was subsequently collected and had a purity of about 98 area percent.

EXAMPLE 4

A five-neck, 5-liter reactor was assembled with a mechanical stirrer, condenser, temperature probe, sampling device, and a continuous feed apparatus for cyclohexyl chloride addition. All reactants were stored over molecular sieve resin, sparged with $N_2$, and the reaction was kept under $N_2$, connected to a bubbler. A total of 1175 grams methyl trimethoxysilane, 284 grams magnesium metal, 120 milligrams iodine, and 90 grams cyclohexyl chloride (10% of the total charge) were added to the reactor under $N_2$. The slurry was brought to reflux. After ~20 minutes, the reaction turned a muddy brown and gas chromatographic analysis showed that the methyl cyclohexyl dimethoxysilane product was forming. The remaining cyclohexyl chloride was slowly added continuously via a transfer tube over about 90 minutes. The brown color continues to deepen and the reaction was allowed to reflux for about 90 minutes after the cyclohexyl chloride addition was complete. Gas chromatographic analysis showed that the methyl cyclohexyl dimethoxysilane area percent was >70%, and the reaction was substantially complete. Methyl cyclohexyl dimethoxysilane was 83 area percent of the final products made (about 1100 grams).

About 1000 grams of hexane was added to the slurry and stirred. The slurry was then transferred through a transfer tube to a filter frit. A second portion of 1000 mls of hexane was added to the reactor and the contents were stirred and then transferred in the same manner to the filter frit containing the filter cake. The desired product was separated from the filtrate by fractional distillation at a head temperature of 198° C. at room pressure. About 90% of the methyl cyclohexyl dimethoxysilane made was collected (~980 grams), as distilled product and it had a purity of 98 area percent by gas chromatographic analysis.

The foregoing is illustrative of certain embodiments of the present invention and should not, therefore, be construed in a limiting sense. The scope of protection that is sought is set forth in the claims which follow.

We claim:

1. A method of forming an alkyl cycloalkyl dialkoxysilane by reacting, with agitation, an alkyl trialkoxysilane with a Grignard reagent which contains a cycloalkyl group which is to be substituted for one of the alkoxy groups of the alkyl trialkoxysilane in the absence of an ether solvent.

2. A method as claimed in claim 1 wherein the cycloalkyl group is cyclohexyl and the alkoxy and alkyl groups are lower alkyl.

3. A method as claimed in claim 2 wherein the alkoxy and alkyl groups are methoxy and methyl, respectively.

4. A method as claimed in claim 3 wherein the reaction is catalyzed by iodine.

5. A method as claimed in claim 4 wherein the reaction is conducted in a hydrocarbon solvent.

6. A method as claimed in claim 1 wherein the Grignard reagent is formed in situ by reaction of a cycloalkylhalide and magnesium.

7. A method as claimed in claim 3 wherein the Grignard reagent is formed in situ by reaction of a cycloalkylhalide and magnesium.

8. A method as claimed in claim 4 wherein the Grignard reagent is formed in situ by reaction of a cycloalkylhalide and magnesium.

9. A method as claimed in claim 1 which is conducted in the substantial absence of solvent.

10. A method as claimed in claim 2 which is conducted in the substantial absence of solvent.

11. A method as claimed in claim 7 which is conducted in the substantial absence of solvent.

* * * * *